United States Patent [19]
O'Lenick, Jr.

[11] Patent Number: 5,843,419
[45] Date of Patent: Dec. 1, 1998

[54] CATIONIC FREE RADICAL POLYMERS

[76] Inventor: Anthony J. O'Lenick, Jr., 743 Ridgeview Dr., Lilburn, Ga. 30047

[21] Appl. No.: 880,091

[22] Filed: Jun. 20, 1997

[51] Int. Cl.⁶ .................................................. A61K 7/075
[52] U.S. Cl. ........................................................ 424/70.11
[58] Field of Search ................................ 424/307, 70.17, 424/70.11

[56] References Cited

U.S. PATENT DOCUMENTS

| | | | |
|---|---|---|---|
| 4,082,701 | 4/1978 | Fries et al. | 526/307 |
| 4,839,166 | 6/1989 | Grollier et al. | 424/70.17 |
| 5,674,478 | 10/1997 | Dodd et al. | 424/70.17 |

FOREIGN PATENT DOCUMENTS

| | | |
|---|---|---|
| 60-240711 | 11/1985 | Japan . |
| 4-16203 | 1/1992 | Japan . |

*Primary Examiner*—Peter F. Kulkosky

[57] ABSTRACT

The present invention deals with the composition, and application of novel compounds, useful as anti-tangle, and conditioning agents for use in personal care, on hair which has been processed. By processes is meant hair which has been subjected to the process of bleaching, relaxing, permanent waving, and/or coloring. These processes make the hair raspy and degrade the properties of the hair. The properties of these novel compounds remediates the damage done to hair and leaves it more manageable and less raspy. The compounds are truly multi-functional, providing softening conditioning, and gloss to treated hair.

10 Claims, No Drawings

CATIONIC FREE RADICAL POLYMERS

BACKGROUND OF THE INVENTION

1. Field of the Invention

The present invention deals with the composition, and application of novel compounds, useful as anti-tangle, and conditioning agents for use in personal care, on hair which has been processed. By processes is meant hair which has been subjected to the process of bleaching, relaxing, permanent waving, and/or coloring. These processes make the hair raspy and degrade the properties of the hair. The properties of these novel compounds remediates the damage done to hair and leaves it more manageable and less raspy. The compounds are truly multi-functional, providing softening conditioning, and gloss to treated hair.

2. Arts and Practices

Human hair has been subjected to several processes which provide an aesthetically appealing property to the hair, but destroy hair structure during processing. The specific processes are coloring, permanent waving, straightening and relaxing. Each of the processes damage hair structure in addition to accomplishing the desired modification of the hair.

The coloring of hair is one of the most important acts of adornment since the origin of man. The most effective coloring preparations on the market today are oxidative dyes. Almost all hair coloring is now performed with oxidation dye, both in the beauty salon and in homes. This type of dye dominates the market because the processes using these materials are quick, and lasting. These materials are called oxidative dyes because the dye must be placed on the hair, penetrate it and be oxidized, most commonly with hydrogen peroxide to make a color.

The dye when applied to the hair must be of low enough molecular weight to penetrate the hair, and be capable of being polymerized in the hair, in the presence of base and hydrogen peroxide, to form larger molecular weight colors. The chemical polymerization in the presence of base and peroxide is a coupling or condensation reaction. The base is an alkaline material selected from the group consisting of sodium hydroxide, potassium hydroxide, calcium hydroxide or the like. The base swells the hair and makes the penetration by the dye more rapid. It also participates in the condensation reaction.

The use of alkaline materials and hydrogen peroxide on the hair has a damaging effect upon the hair. Resulting in physical and chemical damage. However these additives have been necessary to (a) open up the hair to make the penetration of the dye more effective and (b) to condense the dyes. Consequently, prior to the current invention the ability dye hair required base and peroxide.

The process of straightening, relaxing and permanent waving hair make use of alkaline chemicals to swell the hair and change it's properties.

The above processes result in damaged hair. The actual fiber can become raspy. By raspy is meant harsh and dry, and feeling rough. Traditional conditioners which are used on hair generally do not remediate the raspiness and provide soft manageable hair.

Many attempts have been made to obtain a polymeric compound suitable for use on treated hair. We have surprisingly learned that the molecular weight and charge density of the cationic polymer have a profound effect upon the functionality of the cationic conditioner when applied to treated hair.

The references cited herein are incorporated by reference to the extent applicable. Ratios and percentages are by weight and temperatures are Celsius unless otherwise stated.

THE INVENTION

Object of the Invention

It is the object of the current invention to provide a novel series of cationic polymers very well suited to conditioning treated hair. The selection of the proper cationic polymer is based upon (a) the molecular weight of the polymer and (b) the cationic charge density. The molecular weight of the polymers of the present invention are generally below 5,000 AMU. With a molecular weight of under 3,000 being preferred. This molecular weight allows for the polymer to enter the hair fiber and penetrate, providing very effective conditioning. The other aspect of the compounds of the present invention is they are very high in charge density. What this means is that over 85% of the molecule contains groups with cationic charges on them. Each of these factors allow for the selection of a cationic hair care polymer which penetrates the hair and having a high charge density of positive change attracts water, to make the hair more soft, manageable and less raspy.

SUMMARY OF THE INVENTION

The present invention is directed to free radical polymers having a molecular weight below 5,000, and a high degree of cationic charge. The compounds of the invention are prepared by the free radical polymerization of a cationic polymer having a reactive vinyl group.

DETAILED DESCRIPTION OF THE INVENTION

The compounds of the current invention conform to the following generic structure;

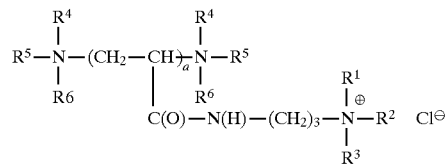

wherein:

R1 and R2 are selected from methyl and ethyl;

R3 is selected from ethyl, methyl and hydrogen;

a is an integer ranging from 10 to 5,000;

$R^4$, $R^5$ and $R^6$ are independently selected from $-(CH_2CH_2O)_x-(CH_2CH(CH_3))_y-(CH_2CH_2O)_zH$ and $CH_3$;

x, y and z are independently 0 to 5.

The compounds of the current invention are prepared by the free radical reaction of a cationic monomer in water in the presence of an amine.

The polymer is made by the free radical polymerization of:

(a) a vinyl amino compound conforming to the following structure

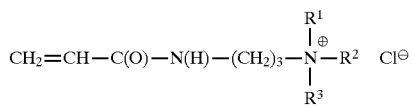

wherein:

$R^1$ and $R^2$ are selected from methyl and ethyl;

$R^3$ is selected from ethyl, methyl and hydrogen;

(b) an amine conforming to the following structure

$R^4$, $R^5$ and $R^6$ are independently selected from $-(CH_2CH_2O)_x-(CH_2CH(CH_3)O)_y-(CH_2CH_2O)_zH$ and $CH_3$;

x, y and z are independently 0 to 5;

and (c) water.

These materials are reacted in water under the influence of a free radical catalyst. Free radical polymerization is well known to those skilled in the art.

Preferred Embodiments

In a preferred embodiment $R^1$ is methyl.
In a preferred embodiment $R^1$ is ethyl.
In a preferred embodiment $R^2$ is methyl.
In a preferred embodiment $R^2$ is ethyl.
In a preferred embodiment $R^3$ is hydrogen.
In a preferred embodiment $R^3$ is methyl.
In a preferred embodiment $R^3$ is ethyl.

17. A polymer of claim 9 wherein the concentration of water ranges from 60 to 80% by weight.

18. A polymer of claim 9 wherein the concentration of water ranges from 70 to 80% by weight.

EXAMPLE

Raw Materials

Class 1 Vinyl Amino Compounds

Example 1–5

$$CH_2=CH-C(O)-N(H)-(CH_2)_3-\overset{R^1}{\underset{R^3}{N^\oplus}}-R^2 \quad Cl^\ominus$$

| Example | $R^1$ | $R^2$ | $R^3$ |
|---|---|---|---|
| 1 | Methyl | Methyl | Hydrogen |
| 2 | Methyl | Methyl | Methyl |
| 3 | Ethyl | Methyl | Hydrogen |
| 4 | Ethyl | Methyl | Methyl |
| 5 | Ethyl | Ethyl | Methyl |

Class 2 Hydroxy Amine Compounds

Example 6–10

The amine reactants conform to the following structure:

$R^4$, $R^5$ and $R^6$ are independently selected from $-(CH_2CH_2O)_x-(CH_2CH(CH_3)O)_y-(CH_2CH_2O)_zH$ and $CH_3$;

x, y, and z are independently 0 to 5.

| | R4 | | | R5 | | | R6 | | |
|---|---|---|---|---|---|---|---|---|---|
| Example | x | y | z | x | y | z | x | y | z |
| 6 | 2 | 0 | 0 | 2 | 0 | 0 | 0 | 0 | 0 |
| 7 | 1 | 0 | 0 | 1 | 0 | 0 | 1 | 0 | 0 |
| 8 | 1 | 1 | 1 | 1 | 1 | 1 | 0 | 0 | 0 |
| 9 | 5 | 5 | 5 | 5 | 5 | 5 | 5 | 5 | 5 |
| 10 | 1 | 1 | 1 | 1 | 1 | 1 | 1 | 1 | 1 |

Preparation of Cationic Polymers

Examples 11–30

General Polymerization Procedure;

The polymerization of the vinyl containing compounds is achieved by utilizing free radical catalyst in a low oxygen containing solvent, most commonly water. The water is deionized and sparged with nitrogen to remove dissolved oxygen contained therein immediately prior to use. Then, the specified amount of the treated deionized water is added to a suitable glass vessel. Most commonly, 60 to 80 % of the total weight of the batch is water. The specified amount of the specified monomers are then added under agitation. Nitrogen is continuously sparged and the temperature is raised to about 50 C. Once the temperature has reached 50 and the nitrogen has been bubbled through the reaction mass for thirty minutes, a free radical initiator is added. Many peracids, like t-butyl-perbenzoate, t-butyl-hydroperoxide and inorganic free radical inatators like stannic chloride can be used. The preferred initator is azobisisobutyl-nitrile. The reaction is exothermic and cooling is used to keep the temperature below 90 C.

The molecular weight is monitored by viscosity and both increase as the reaction continues.

Example 11

To the specified number of grams (5,000 Gm.) of deionized water, which has just been sparged with nitrogen for 30 minutes, is added the specified amount (900 grams of vinyl amino compound (Example #1). Next add the specified amount 80 grams) of Amine compound (Ex #6), under good agitation and nitrogen sparge. The temperature is raised to about 50 C. Once the temperature has reached 50 and the nitrogen has been bubbled through the reaction mass for thirty minutes, the specified amount of the specified catalyst (azobisisobutylnitrile) is added. The catalyst may be optimally added in smaller increments of one quarter of the total needed waiting 30 minutes between additions. The viscosity will raise as the polymerization occurs. The temperature raises to about 90 C. and is cooled with cooling water as needed to prevent the temperature from reaching 90 C. The desired polymer is used as prepared.

Examples 12–30

The above procedure is repeated only substituting the specified amount and type of monomer, catalyst and water specified.

| | Vinyl Amino Compound | | Amino Compound | |
|---|---|---|---|---|
| Example | Example | Grams | Example | Grams |
| 12 | 2 | 900.0 | 6 | 80.0 |
| 13 | 3 | 900.0 | 7 | 80.0 |
| 14 | 4 | 900.0 | 8 | 80.0 |
| 15 | 5 | 900.0 | 9 | 80.0 |
| 16 | 1 | 900.0 | 10 | 200.0 |
| 17 | 2 | 900.0 | 5 | 200.0 |
| 18 | 3 | 900.0 | 6 | 200.0 |
| 19 | 4 | 900.0 | 7 | 200.0 |
| 20 | 5 | 900.0 | 8 | 200.0 |
| 21 | 1 | 900.0 | 9 | 200.0 |
| 22 | 2 | 900.0 | 10 | 200.0 |
| 23 | 3 | 900.0 | 5 | 900.0 |
| 24 | 4 | 900.0 | 6 | 900.0 |
| 25 | 5 | 900.0 | 7 | 900.0 |
| 26 | 1 | 900.0 | 8 | 900.0 |
| 27 | 2 | 900.0 | 9 | 900.0 |
| 28 | 3 | 900.0 | 10 | 900.0 |
| 29 | 4 | 900.0 | 6 | 50.0 |
| 30 | 5 | 900.0 | 7 | 50.0 |

Applications Data

Applications of the Compounds of The Invention Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water, and exposed to Calcium Hydroxide based commercial relaxer, following the label instructions The hair is then squeezed out and while still damp dipped into a 200 ml solution of 0.2 % active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12–14 seconds.

| Rinse Conditioner (Wet Comb Out Test) | |
|---|---|
| Product | Time in Seconds |
| Product Example # 20 | 11 |
| Product Example # 15 | 13 |
| Stearyldimethylbenzyl ammonium chloride | 12 |

The compounds were also evaluated for softness. The scale used was 1 for raspy hair to 5 for very soft conditioned hair.

The results were as follows:

| Product | Softness |
|---|---|
| Product Example # 20 | 5 |
| Product Example # 15 | 4 |
| Stearyldimethylbenzyl ammonium chloride | 2 |

The compounds of the present invention are useful as softening, anti-tangle, and conditioning agents for treated hair.

What is claimed:

1. A polymer composition made by the free radical polymerization of:

(a) a vinyl amino compound conforming to the following structure

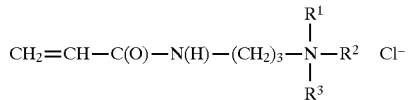

wherein:
$R^1$ and $R^2$ are selected from methyl and ethyl;
$R^3$ is selected from ethyl, methyl and hydrogen;

(b) in the presence of an amine conforming to the following structure;

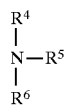

$R^4$, $R^5$ and $R^6$ are independently selected from $-(CH_2CH_2O)_x-(CH_2CH(CH_3)O)_y-(CH_2CH_2O)_zH$ and $CH_3$;

x, y and z are independently 0 to 5; and (c) water, said composition being useful as a softening, anti-tangle, and conditioning agent for treated hair.

2. A polymer composition of claim 1 wherein $R^1$ is methyl.

3. A polymer composition of claim 1 wherein $R^1$ is ethyl.

4. A polymer composition of claim 1 wherein $R^2$ is methyl.

5. A polymer composition of claim 1 wherein $R^2$ is ethyl.

6. A polymer composition of claim 1 wherein $R^3$ is hydrogen.

7. A polymer composition of claim 1 wherein $R^3$ is methyl.

8. A polymer composition of claim 1 wherein $R^3$ is ethyl.

9. A polymer composition of claim 1 wherein the concentration of water ranges from 60 to 80% by weight.

10. A polymer composition of claim 1 wherein the concentration of water ranges from 70 to 80% by weight.

* * * * *